(12) United States Patent
Cairns

(10) Patent No.: US 8,476,462 B2
(45) Date of Patent: Jul. 2, 2013

(54) SULFONYL CYANINE DYES AND DERIVATIVES

(75) Inventor: Nicholas Cairns, Los Altos, CA (US)

(73) Assignee: Combinix, Inc., Sunnyvale, CA (US)

( * ) Notice: Subject to any disclaimer, the term of this patent is extended or adjusted under 35 U.S.C. 154(b) by 822 days.

(21) Appl. No.: 12/191,937

(22) Filed: Aug. 14, 2008

(65) Prior Publication Data
US 2010/0041901 A1   Feb. 18, 2010

(51) Int. Cl.
*C07D 401/06* (2006.01)
(52) U.S. Cl.
USPC ........................................... 548/455
(58) Field of Classification Search
USPC ........................................... 548/455
See application file for complete search history.

(56) References Cited

U.S. PATENT DOCUMENTS 3,745,015 A * 7/1973 Van Pee et al. ............... 430/567

* cited by examiner

*Primary Examiner* — Joseph Kosack
(74) *Attorney, Agent, or Firm* — Combinix, Inc.; Nicholas Cairns

(57) ABSTRACT

Fluorescent cyanine and squaraine dyes are described that can be conjugated to analyte molecules of interest such as peptides, proteins, nucleic acids, RNA, DNA, carbohydrates, polymers and small molecules via a sulfonyl or sulfonamide substituent. The new dyes are made via a novel cyanine dye activation procedure that converts the normally stable, water solubilizing sulfonate substituents into a reactive sulfonyl halides. The sulfonyl halides may be directly conjugated to analytes or can be further converted to more stable reactive sulfonamide handles or to water soluble sulfonamides. The general structure of the new dyes is given below where the central linker is an unsaturated carbon chain or an unsaturated chain containing a squaraine moiety.

10 Claims, 1 Drawing Sheet

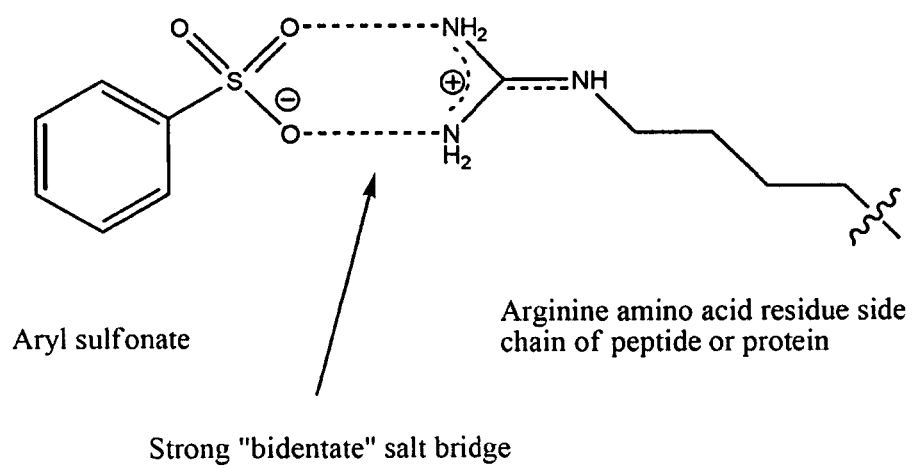
Aryl sulfonate
Arginine amino acid residue side chain of peptide or protein
Strong "bidentate" salt bridge
Strong interaction between any aryl sulfonate (negatively charged) and any arginine amino acid residue (positively charged) with a bidentate salt bridge.

US 8,476,462 B2

SULFONYL CYANINE DYES AND DERIVATIVES

The U.S. Government has a paid-up license in this invention and the right in limited circumstances to require the patent owner to license others on reasonable terms as provided for by the terms of Grant No. 5R44CA093099-03 awarded by the National Cancer Institute, National Institutes of Health, Bethesda Md.

FIELD OF THE INVENTION

The present invention relates to fluorescent cyanine dye compounds and more particularly to fluorescent cyanine dye compounds that have aromatic sulfonic acid derived functionality.

CROSS-REFERENCES TO RELATED MATERIALS

This application incorporates by reference in their entirety for all purposes all patents, patent applications (published, pending, and/or abandoned), and other patent and nonpatent references cited anywhere in this application. The cross-referenced materials include but are not limited to the following publications: Richard P. Haugland, HANDBOOK OF FLUORESCENT PROBES AND RESEARCH CHEMICALS (6$^{th}$ Ed. 1996); Joseph R. Lakowicz, PRINCIPLES OF FLUORESCENCE SPECTROSCOPY (2$^{nd}$ Ed. 1999); Richard J. Lewis, Sr., HAWLEY'S CONDENSED CHEMICAL DICTIONARY (12$^{th}$ Ed. 1993); Michael B. Smith and Jerry March, MARCH'S ADVANCED ORGANIC CHEMISTRY (6$^{th}$ Ed. 2007); A. I. Vogel, A. R. Tatchell, B. S. Furnis, and A. J. Hannaford, VOGEL'S TEXTBOOK OF PRACTICAL ORGANIC CHEMISTRY (5th Ed. 1996); W. T. Mason, FLUORESCENT AND LUMINESCENT PROBES FOR BIOLOGICAL ACTIVITY (1993); Jeremy M. Berg, John L. Tymoczko, and Lubert Stryer, BIOCHEMISTRY (6$^{th}$ Ed. 2006); Greg T. Hennanson, BIOCONJUGATE TECHNIQUES (1996).

BACKGROUND OF THE INVENTION

Fluorescent molecules have been known for more than 100 years in the art and have become increasingly important for the detection of small molecule, biomolecule, polymer and other analytes when covalently or otherwise associated with such analytes. Fluorescent entities are now frequently used in high throughput drug discovery screening in the pharmaceutical, agrochemical, cosmetic, polymer and biotechnology industries and in many cases taking the place of the environmentally unfriendly and undesirable radioimmunoassay (RIA) that necessitates the controlled use and disposal of radioactive materials. The fluorescent assay often shows improved sensitivities over the equivalent RIA assay and is of course much safer and simpler for laboratory workers to execute. Examples of fluorescent techniques in these industries are; conventional fluorescence and luminescence assays, ELISA (Enzyme-linked immunosorbent assay) fluorescence polarization assays, fluorescence resonance energy transfer (FRET) assays and fluorescence activated cell sorting (FACS) procedures. Traditionally, fluorescent reporter molecules in the above applications have had several undesirable properties. Most dyes are very hydrophobic or contain bare sulfonate groups ($Ar-SO_3^-$) that are responsible for a high level of non-specific binding to proteins and peptides. Hydrophobic dyes or dyes containing bare aromatic sulfonate substituents form aggregates that are responsible for many undesirable effects such as self-quenching or absorbance emission shifts, Many traditional dyes such as fluorescein have limited pH dependent water solubilities and absorption/emission wavelengths in the 350-500 nm range of the electromagnetic spectrum. This is not the most convenient wavelength range with which to monitor biological systems as a host of biological molecules also absorb light in this region, for example, hemoglobin. At pH 7, the absorbance maximum of fluorescein occurs at 490 nm and emission is at around 515 nm. A much better range is 550-850 nm where the biological absorption window and autofluorescence is at a minimum. In the near-infrared region of the electromagnetic spectrum above 850 nm, water starts to absorb very strongly, dramatically lowering dye sensitivity. Also, traditional dyes such as fluorescein and rhodamine are less photostable than many of the longer wavelength absorbing dyes particularly when intense excitation is required such as in fluorescence microscopy, in part, due to their inherent "higher energy" absorption at shorter wavelengths.

Novel fluorescent dyes that operate in the visible/near infra-red (NIR) region of the electromagnetic spectrum have been shown to act as excellent reporter components of targeting molecular probes and tracers. However, many of the available dyes have undesirable properties such as relatively high non-specific binding and a tendency to aggregate. The main focus of this patent is the discovery of novel cyanine dyes for use in high throughput screening, fluorescence polarization, biomedical imaging and other applicable techniques such as immunofluorescence microscopy and fluorescence activated cell sorting and counting. The new dyes are designed to have much improved properties to function in biological systems, the main improvement being the use of more appropriate positively charged water solubilizing groups that improve sensitivity in proteinaceous assays and reduce dye aggregation. The new dyes are designed to absorb in the long visible near-infrared region between 550 and 850 nm. The dyes have high molar extinction coefficients of over 100,000 $M^{-1}cm^{-1}$; this is a measure of how efficiently the dyes absorb light of a particular wavelength, the higher the molar extinction coefficient, the higher the efficiency of light absorption. The bench standard, fluorescein, has an extinction coefficient of 80,000 $M^{-1}cm^{-1}$ above 6 in water or methanol. Extinction coefficients are routinely measured in the laboratory using UV/Visible spectrophotometers. Many of the biotechnological and pharmaceutical companies have an in-house chemical library of compounds, many of these compounds themselves absorb light up to around 600 nm where the commonly used shorter wavelength dyes such as fluorescein and rhodamine dyes operate making them much less efficient than a longer wavelength dye absorbing light above 600 nm.

Whole animal cellular and molecular imaging has the potential to dramatically accelerate drug discovery and development by revolutionizing in vivo research. As with all imaging techniques, animals do not have to be sacrificed at each data collection point and they can therefore serve as their own controls. Also, the instrumentation is relatively low cost, can be computerized so more data can be collected at more frequent time points. In 1995, Christopher H. Contag and co-workers described a method for noninvasive optical monitoring of microbial infections in a whole animal. Their model system began with infection of mice with strains of the bacterial pathogen *Salmonella typhimurium* which were modified to produce bioluminescence via the luciferin/luciferase mechanism. This was effected by constitutive expression of a luciferase enzyme from the soil bacterium *Photorhabdus luminescens*. *Salmonella typhimurium* is an intracellular pathogen of mice, humans and other animals which initially infects the intestinal mucosa after oral ingestion. It then spreads systemically largely by unknown mechanisms to many sites within the host. The authors used a modified near infrared CCD camera to detect light emission from the bacterium. They discovered that the highest intensity emission came from the caecum where the bacteria appeared to gather before assaulting other tissues. They went on to perform qualitative real time studies on the efficacy of administered antibiotics and witnessed rapid clearance of fully virulent bacterial strains by naturally bacterial resistant mouse strains. These initial experiments were reported to be somewhat hindered by the requirement of oxygen for the intracellular light producing reaction and more so by the short 486 nm wavelength emission of the bioluminescent system. Due to the short wavelength of the emitted light, much of the light was absorbed by the animal's own tissue and plasma components such as hemoglobin. Tumor imaging work using labeled tumor targeting antibodies confirmed that further red-shifted dyes were far superior to fluorescein for biomedical "whole body" imaging as they had lower backgrounds, better circulating lifetimes and were able to emit light that penetrated further through general tissue due to much less interference from the animal's own tissue and plasma components. The new cyanine dyes could be used as reporter groups in these kinds of experiments.

There are currently two types of whole body optical imaging, the first, bioluminescent imaging, is where a light emitting gene system is introduced into the animal such as the luciferase/luciferin system or green/red fluorescent proteins. The second type is where a fluorescent tracer molecule is used and external light is required. The first emits its own light but requires a plentiful supply of oxygen and cannot be used above 600 nm. This is a severe limitation as much of the light is lost due to poor tissue penetration as described above. The second "red-shifted" fluorescent tracer method is increasingly being used and emitted light can easily penetrate to tissue depths sufficient for good clinical imaging in small rodents such as mice. Developments in imaging technologies have had a profound impact on clinical medicine including, ultrasound scanning, magnetic resonance imaging, x-ray computed tomography and nuclear tomography imaging. These systems are primarily used for displaying anatomical, physiological and metabolic parameters but they are increasingly being used in experimental animal systems for imaging at the cellular and molecular levels in vivo. These currently used imaging systems are well developed but rely on physical parameters and properties to generate image contrast such as, sound impedance, electromagnetic wave impedance or nuclear alignments. Methods that involve X-rays are also inherently unsafe in that prolonged exposure to X-rays is known to cause cancer. In vivo fluorescence imaging offers very safe, more sensitive early stage detection of tumors or enzymes that would be difficult to achieve with existing imaging techniques.[15]

Fluorescent tracer molecules are commonly used as tools for in vivo imaging. The tracer molecule is composed of two parts, a targeting moiety which is typically an antibody, peptide or DNA oligomer, and a reporting component which, in fluorescent imaging, is a fluorescent molecule. For tumor imaging for example, the targeting component could be an antibody or peptide that is known to bind more specifically to the tumor cells than to normal host cells. Tumor cells often over-express certain surface proteins or particular receptors that targeting antibodies can be raised against. Certain cancers such as head, neck and oral cancers are known to greatly over-express the EGF receptor, a 170 kDa glycoprotein with tyrosine kinase activity and again, antibodies or peptides have been used to target these tumors. Weissleder recently introduced new targeting concepts by developing protease activated near-infrared fluorescent probes for tumor detection and for receptor imaging using a targeting fluorescent peptide.

A variety of other techniques would benefit from the discovery of efficient long wavelength, near-infrared dyes. For example, immunofluorescence microscopy is an indispensable tool in cell biology, microbiology and histology. It provides for specific visualization of a particular protein or other biological target of interest in live or fixed cells while all other biomolecules remain invisible. Traditionally, the shorter wavelength dyes fluorescein and rhodamines (490-590 nm) have been used in this area but autofluorescence from unlabeled biomatter significantly lowers these probes sensitivity. Paraformaldehyde fixing of tissues also causes an increase in the inherent tissue autofluorescence in this range. Another use for the dyes being made in this project is in the area of fluorescence activated cell sorting or FACS. FACS machines have been used for some time to rapidly quantify molecular events in cells. This technique has also been used in screening solid phase chemical libraries where the fluorescently labeled antibodies or enzymes bind to resin bound test peptides or small molecules on the bead surface. Many new whole cell assay procedures are now being developed on these machines where the cells or beads are just being counted, not sorted. The fluorescent event, which could be either a simple receptor or antibody binding event or it could be a fluorescent enzyme assay, either occurs in the cell or does not occur and is rapidly detected and counted by the FACS machine. This field has undoubtedly been driven by the incredibly low cost of some the new cell counting machines. This patent describes a series of novel long wavelength dyes for potential use in the above applications.

The prior art recites cyanine dyes both with and without sulfonic acid or sulfonate groups ($SO_3H$ and $SO_3^-$, where negatively charged sulfonate groups are used both as water solubilizing groups and for the purpose of enhancing the fluorescence properties of the dyes see Waggoner U.S. Pat. No. 5,268,486, Ahlem in U.S. Pat. No. 5,955,612 and WO09641174 and Terpetschnig in U.S. Pat. No. 6,538,129 B1 and U.S. Pat. No. 7,250,517 B2 and references cited therein).

SUMMARY OF THE INVENTION

The invention provides fluorescent compounds containing two flanking groups of the general formula:

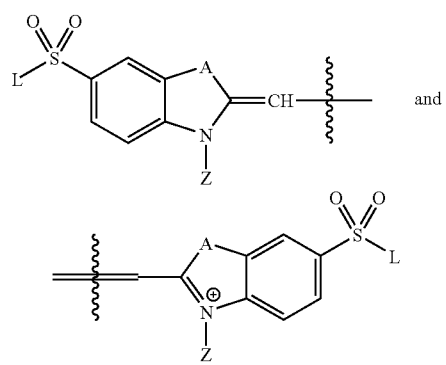

that are linked together by the following central linkers:

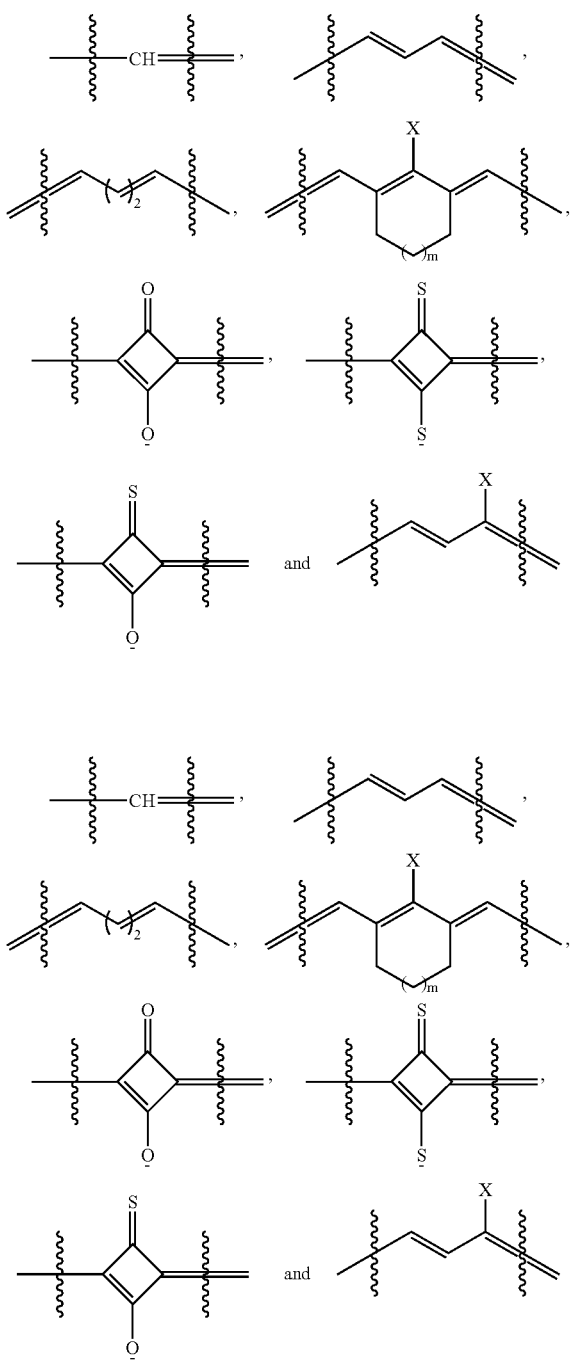

L can be a handle to link to an analyte of interest or a positively charged water solubilizing group such as a primary, secondary tertiary amine or quaternary amine or can be a reactive leaving group such as Cl or Br. Such positively charged water solubilizing groups have a distinct advantage over the normally used sulfonate waster solubilizing groups in that the positively charged groups are much less prone to non-specific binding than the sulfonate groups (see FIG. 1). This is due to the positive charge on the nitrogen being shielded by the three or four alkyl groups that are attached to the nitrogen rather than being on terminal atoms as is the case with the negative charge of the sulfonates.

BRIEF DESCRIPTION OF THE DRAWINGS

FIG. 1 shows how a dye containing a free sulfonic acid moiety can bind very strongly with an arginine residue of any peptide or protein via a strong pseudo bidentate salt bridge. Such free sulfonates can also bind strongly to any areas of positive charge on any molecule, for example to lysine residues in peptides and proteins. A further disadvantage of negatively charged sulfonate based dyes is that they do not easily cross negatively charged phosphate cell membranes and therefore may prevent an analyte from entering cell in say a cell based biological assay. It is well known in the art that sulfonate residues on solid phase polymers (strong cation exchange resins) are often used to purify peptides and proteins by directly binding with areas of positive charge and especially with arginine amino acid residues. The peptides or proteins are first bound on a resin column where all the impurities pass through the column and then are released from the resin column by adjusting the pH to remove the positive charge on the peptide or protein or by increasing the salt concentration.

DETAILED DESCRIPTION OF THE INVENTION

The present invention relates to compounds that are useful as fluorescent reporter molecules in biological assays for drug discovery or for the discovery of other biologically active molecules, high throughput screening, biomedical optical imaging, fluorescent microscopy, fluorescence activated cell sorting and as fluorescent markers for protein identification in gel electrophoresis. The invention also relates to chemical intermediate compounds to the fluorescent compounds and to the methods for making all of the compounds. Fluorescent reporters are usually chemically conjugated to a biological molecule or analyte of interest, usually via an amide or thioamide linkage. This necessitates that the fluorescent reporter have either a carboxylic acid or activated version, a sulfonyl chloride or other halide or a cyanate or thiocyanate for linking to a biological molecule that has a primary or secondary amino group or analytes that contain a carboxylic acid group. The covalent linkage can also be made to a thiol-containing biological molecule or analyte by modifying the fluorescent molecule so that it contains an iodo, bromo or chloroacetamide, a maleimide or an alpha beta unsaturated carbonyl group (Michael acceptor). The covalent linkage can also be in the form of a phosphoramidite for incorporation into to nucleic acids, oligonucleotides or nucleosides. The covalent linkage can also be made from one component (the fluorescent reagent or the analyte) being an aldehyde and the other component being a hydrazine or hydrazide so as to form a hydrazone linkage.

The invention provides fluorescent compounds with appropriate linking handles attached to a sulfonyl group (Ar—SO$_2$—) on the dye carbocycle to couple to a wide range of biologically active molecules. The linking handle comprises of a molecule having at least two functional groups. One of the functional groups attaches to the sulfonyl group on the dye and the other functional group attaches to an analyte molecule of interest or can be further modified so that it can react and covalently link to an analyte molecule. In a preferred embodiment one to six linking groups contain an amine functionality that can form one to four polar sulfonamide groups with cyanine type dyes that contain one to four activated sulfonyl groups. The linking moiety also must contain a variety of well-established linking chemical handles (for example another amine, an activated or unactivated carboxylic acid, an alkyl halide, a haloacetamide, a maleimide, an aldehyde, a hydrazine, an alkene or a phosphoramidne) that can be linked to an analyte, biochemical molecule or other molecule of interest. The linking handle may contain a straight alkyl chain, an oligoethylene glycol component (see example 6), an aromatic or heteroaromatic group or an alicyclic group such as cyclohexane (a typical linker here would be cis or trans-1,4-diaminocyclohexane). In another embodiment there is no linking group from the sulfonyl group, the sulfonyl chloride itself is the active linking group (for example the bis sulfonyl chloride compound in example 1 below can act as a bifunctional or mono functional fluorescent moiety in its own right depending on the stoichiometry of active dye to analyte and on the reaction conditions—if water is present this can deactivate one of the sulfonyl chloride groups making it a monofunctional reagent).

The use of the new dyes follows well established literature procedures in the art, for example when using sulfonyl halides, the dyes should be combined in an appropriate ratio of dye to a suitable nucleophilic analyte for labeling (for example, a primary amine) in a solvent such as dimethylformamide (DMF) containing appropriate equivalents of a base such as triethylamine (TEA) or sodium hydroxide at around −5 to 150 degrees centigrade depending on the relative stability of the dye and analyte. The base should be added to produce the free amino group for the duration of the reaction and to mop up hydrogen halide liberated from the sulfonyl halide and proton on the primary amine. Dyes with N-hydroxysuccinimide groups can be conjugated to primary amine groups using the same conditions described above only keeping the of the mixture between 7 and 9.5. Such conjugations and those of other reactive handles described in this patent are very well know in the art.

Reactive handles on one (monofunctional dyes) or both (bifunctional dyes) sulfonyl or sulfonamide residues can include amine reactive handles such as carboxylic acids, that can be coupled to amines, alcohols or phenols with well known coupling agents such as carbodiimides (e.g., dicyclohexylcarbodiimide or EDC—a water soluble carbodiimide), HBTU, TBTU, or other well known carboxyl activating agents. The dye carboxylic acid group can also be pre-activated for example, by forming acid halides, cyanates, thiocyanates, NHS esters, HOBT esters, symmetrical and unsymmetrical anhydrides. Carboxyl reactive dyes have primary amines, alcohols or phenols and in this case the dyes are not activated as such, the analyte carboxylic acid has to be first activated as above and then will react with the amino dye component to form a covalent amide or ester. Other active handles include, aryl azides to form covalent bonds with an analyte upon exposure to light, haloacetamides, Michael acceptors and maleimides for conjugation to thiols, phosphoramidites to conjugation to nucleic acids.

EXAMPLES

Example 1

Phenylhyrazine-4-sulfonic acid is commercially available from a number of fine chemical suppliers. 5 g of Phenylhyrazine-4-sulfonic acid was treated with 3-methyl-2-butanone (15 mL) in acetic acid (AcOH, 20 mL) and refluxed for 3 h. On cooling, 2,3,3-trimethylindolenine-5-sulfonic acid precipitated out and was filtered, washed with a little diethyl ether and dried.

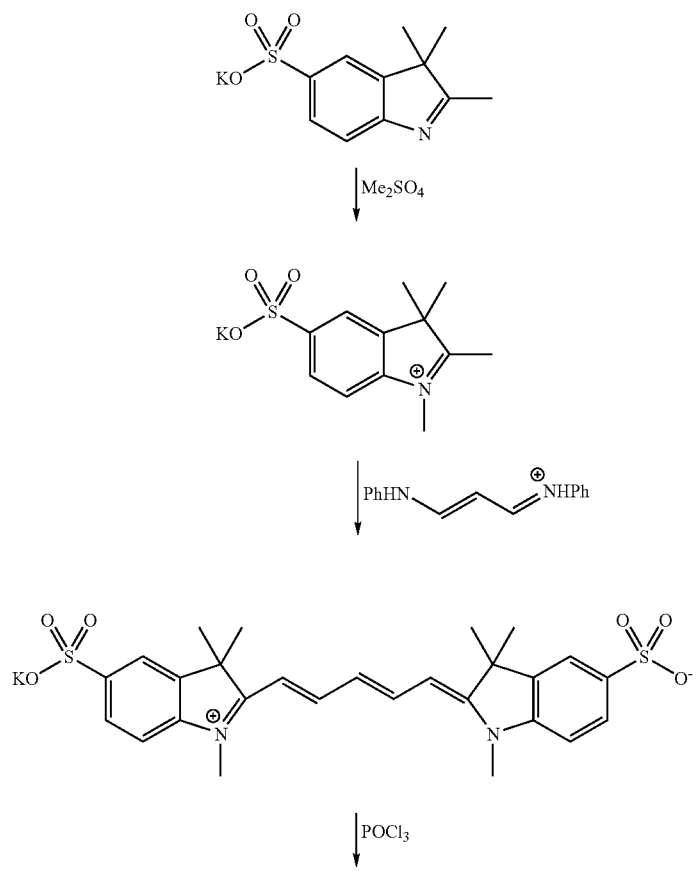

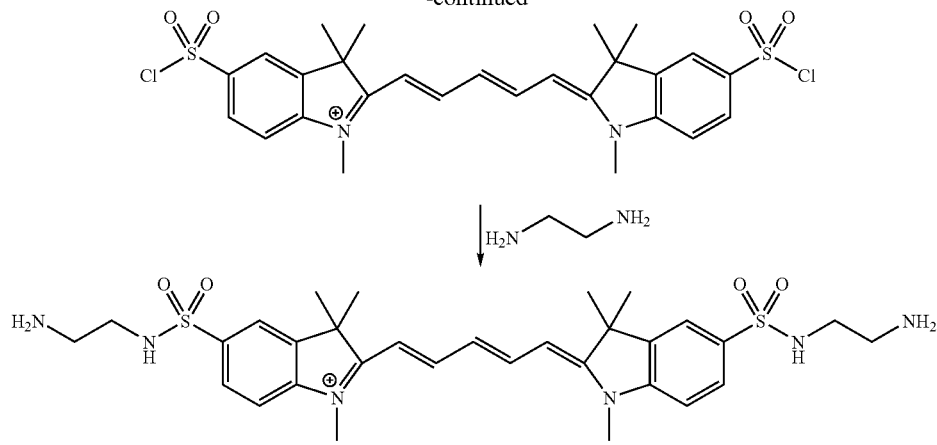

The free base of was then formed by the addition of potassium hydroxide in 2-propanol. This was then refluxed with dimethylsulfate for 3 h to afford after removal of the solvent, the N-methyl compound. This was then treated with malonaldehyde bisphenylimine (0.3 equivalents) and refluxed in an acetic anhydride/pyridine mixture (4:1, 10 mL) for 1 h until a deep blue solution formed. The solvent was removed on a rotary evaporator and the crude dye was purified by flash chromatography on silica gel eluting with a gradient of methylene chloride and methanol (A=methylene chloride, B=methanol, gradient was 0 to 100% B over 30 minutes) to afford 0.4 g of the his sulfonic acid. This was then refluxed with $POCl_3$ for 2 h to form a key bis sulfonyl chloride intermediate that can also be used in its own right as a bifunctional sulfonyl chloride dye for labeling analytes or biomolecules that contain primary or secondary amines or alcohols and also phenols (Ar—OH). 200 mg of this compound was treated with an excess of ethylenediamine (1 g) in dimethylformamide for 5 minutes at 5° C. and the solvent was evaporated under vacuum. The residue was then acidified with trifluoroacefic acid (TPA) and subjected to flash chromatography on silica gel with a gradient of methylene chloride and methanol (A=methylene chloride, B=methanol, gradient was 0 to 100% B over 30 minutes) to afford 1 g of the bifunctional amino dye.

Example 2

Monofunctional and Bifunctional "Amino Reactive" Carboxylic Dye

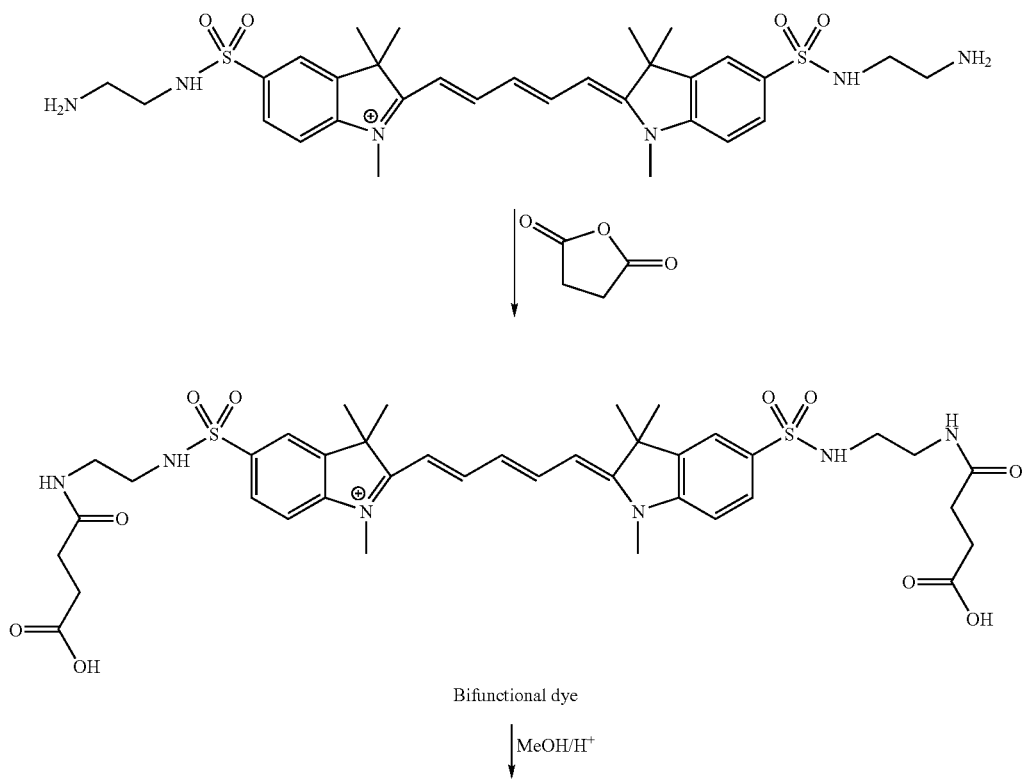

-continued

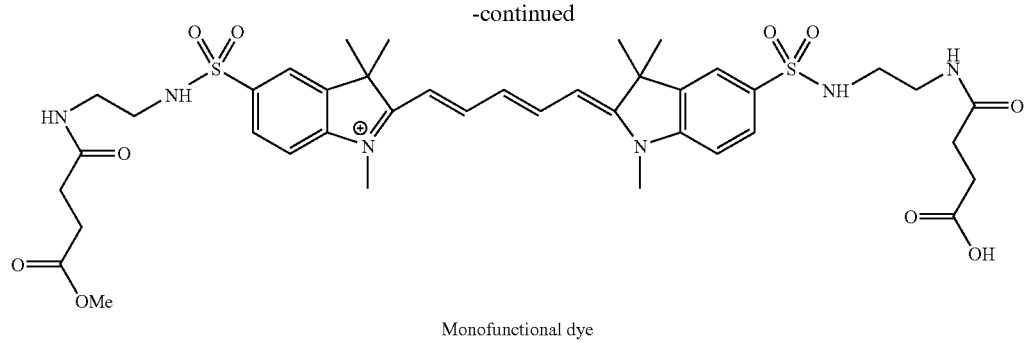

Monofunctional dye

The bis amino dye from example 1 was treated with 50 mg with succinic anhydride (100 mg) and then purified by flash chromatography with a gradient of methylene chloride and methanol (A=methylene chloride, B=methanol, gradient was 0 to 100% B over 30 minutes) to afford 20 mg of compound the bis carboxylic dye. This compound could be activated to give a bifunctional NHS activated carboxyl dye by treatment with N-hydroxysuccinimimde and a carbodiimide in the usual manner. It was also treated with methanol and dry HCl for 2 minutes at 5° C. to give the mono methyl ester/carboxylic acid dye (a monofunctional "amino-reactive" dye).

Example 3

Preparation of a Monofunctional Amino and a Monofunctional Carboxyl Cyanine Dye

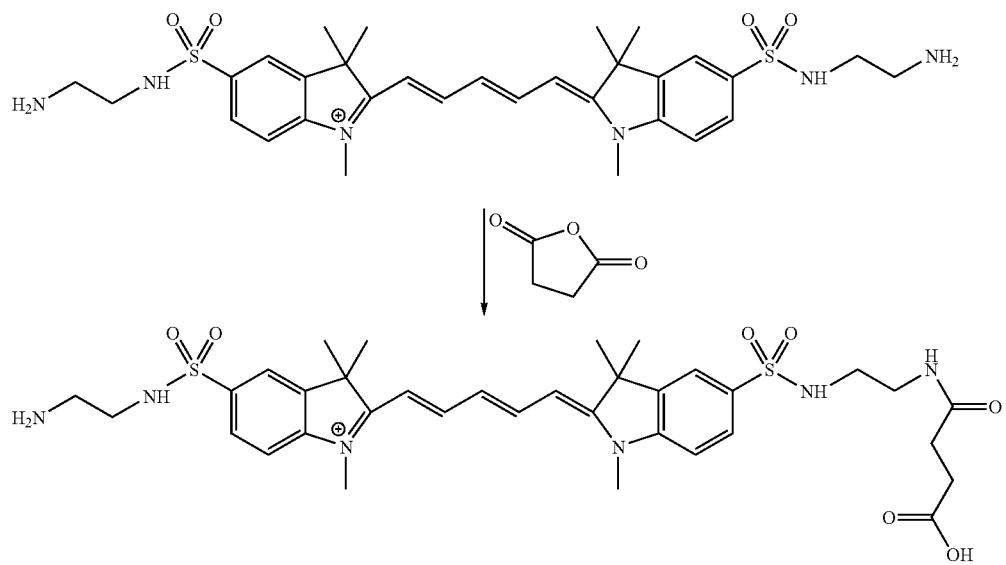

he bis amino dye was treated with one half equivalent of succinic anhydride in DMF and then purified by HPLC chromatography to give the amino carboxylic acid dye above that can be used as a monofunctional amine dye or on protection of the amino group, a monofunctional carboxylic acid dye.

Example 4

The bis sulfonyl chloride was treated with a mixture of ethylene diamino and N,N-dimethyl ethylene diamino (1:10) in DMF at 5° C. to yield a mixture of the amino/dimethylamino and the his dimethylamino dyes (together with some of the his amino dye). The mixture was purified by reverse phase HPLC.

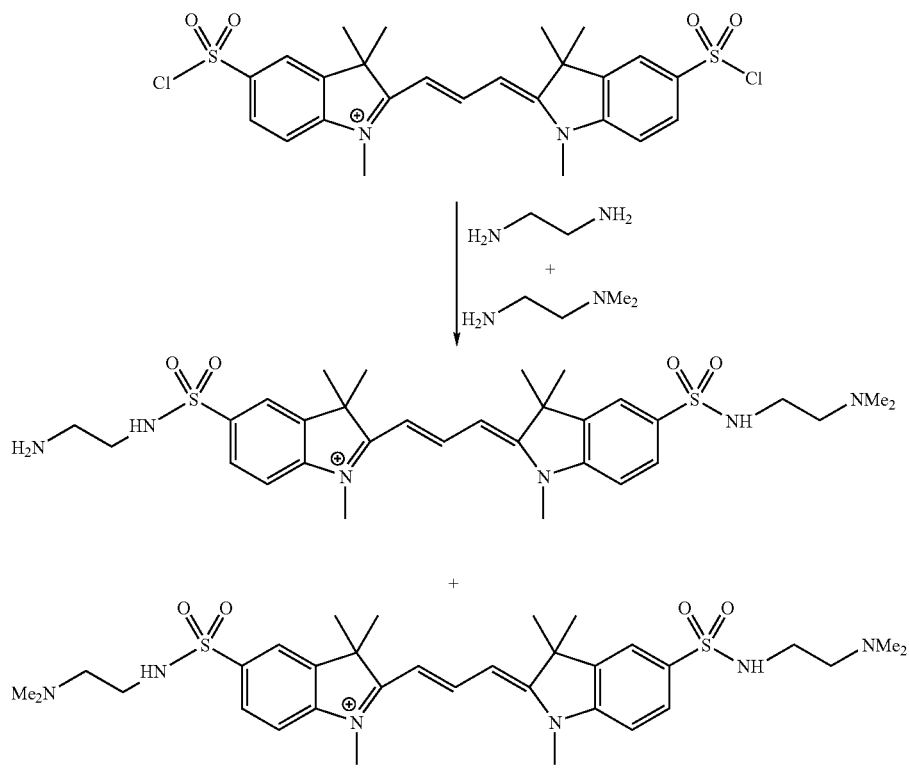
Example 5
A number of substituted phenols were added to the bis sulfonyl chloride dye below to give in DMF with triethylamine as a base to give stable sulfonate ester dyes as products. The R substituents were H, alkyl, aryl, alkyl carboxylates, alkyl amines and other functional groups. The aryl group can also be any heterocyclic aromatic moiety.
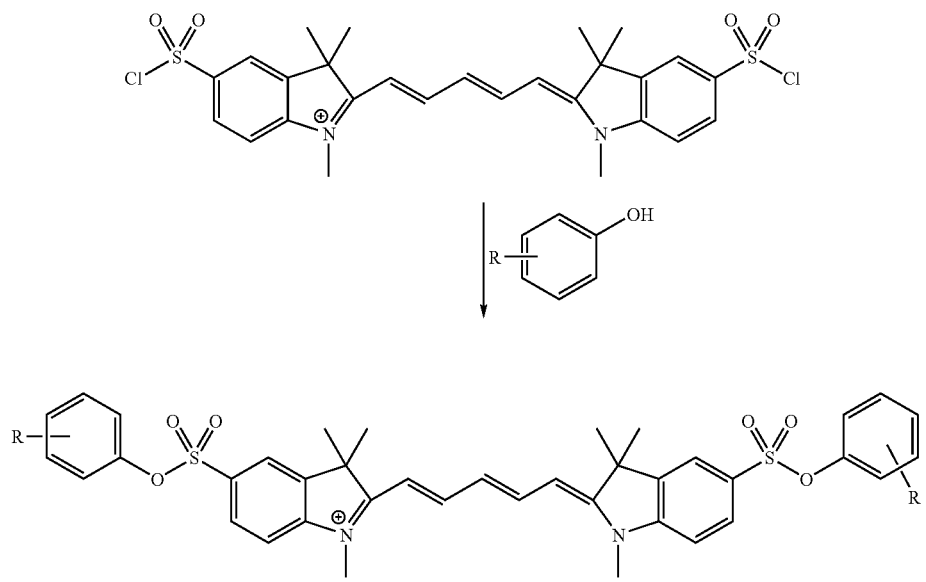

The R group may contain a reactive chemical handle such as an NHS ester, acid chloride, thiocyanate, cyanate for conjugation to a primary amine or alcohol. It may also contain an amine for conjugation to a carboxylic or acid or sulfonyl halide or an iodo or bromoacetamide or maleimide for conjugation to a free thiol or a phosphoramidite for conjugation to nucleic acids, nucleosides or nucleotides.

Example 6

The bis sulfonyl chloride below was treated with a mixture of 2,2'(ethylenedioxy)diethylamine and N,N-dimethyl ethylene diamino (1:10) in DMF at 5° C. to yield a mixture of the amino dimethylamino and the his dimethylamino dyes (together with some of the his amino dye). The mixture was purified by reverse phase HPLC in the usual manner

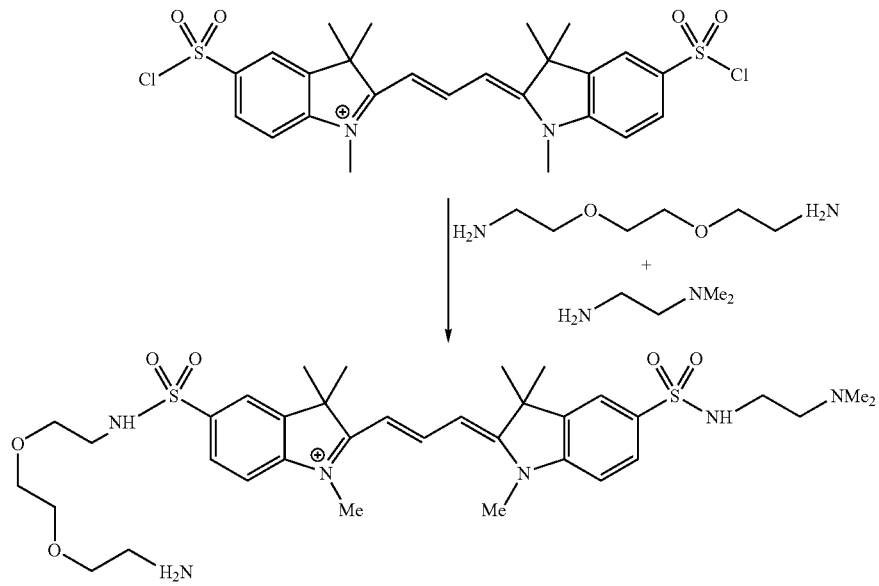

What is claimed is:

1. A composition of matter comprising a fluorescent compound

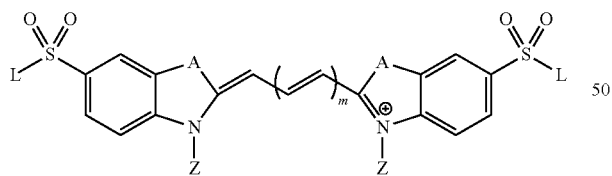

wherein:

$m$ is 1 or 2;

A is independently selected from the group consisting of O, Se, Te and $CR_2$ wherein, R is independently selected from the group consisting of Me, Et, $C_3$-$C_{16}$ alkyl, alkyl ether groups and oligo ethylene glycol groups containing 2 to 20 oxygen atoms;

Z is independently selected from the group consisting of Me, Et, and $C_3$-$C_{16}$ alkyl;

L is independently selected from the group consisting of F, Cl, Br, O-aryl,
—NH—(Y)—$NR_2$ and —NH—(Y)—NR—CO—(Y)—COT wherein, Y is selected from the group consisting of a $C_1$-$C_{18}$ alkyl chain, an ether linkage, an aromatic linkage, $C_1$-$C_{12}$ cycloalkyl and an oligoethylene glycol linkage containing 2 to 20 oxygen atoms, R in this instance is independently selected from the group consisting of H, Me, Et, and $C_3$-$C_{16}$ alkyl;

and wherein T is independently selected from the group consisting of OH, Cl, Br, O—($C_1$-$C_{16}$) alkyl, O-aryl, N-hydroxysuccinimide ester, hydroxybenzotriazole ester, haloalkylacetamide, —NH-maleimide, thiocyanate, cyanate, phosphoramidite, symmetrical anhydrides and unsymmetrical acid anhydrides.

2. The composition of claim 1 wherein said fluorescent compound is

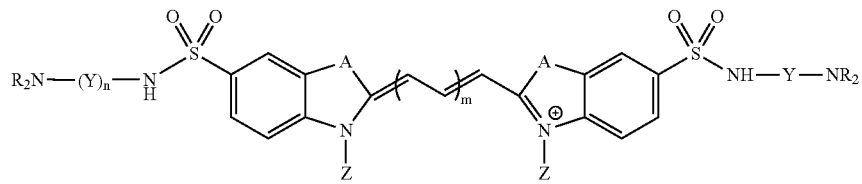

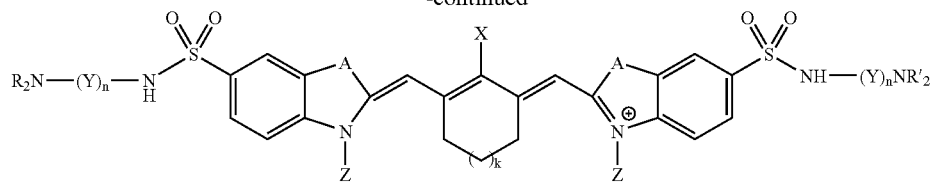

wherein:
- m is 1 or 2;
- A is independently selected from the group consisting of O and CMe₂;
- Z is independently selected from the group consisting of Me, Et, and $C_3$-$C_8$ alkyl;
- Y is selected from the group consisting of a $C_1$-$C_{18}$ alkyl chain, an ether linkage, an aromatic linkage, $C_1$-$C_{12}$ cycloalkyl and an oligoethylene glycol linkage containing 2 to 20 oxygen atoms,
- R in this instance is independently selected from the group consisting of H, Me, Et, and $C_3$-$C_{16}$ alkyl.

3. A composition of matter comprising

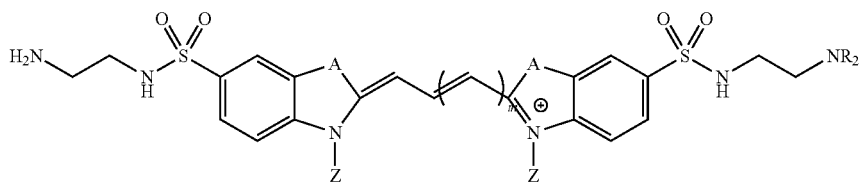

wherein:
- m is 1, 2 or 3;
- A is independently selected from the group consisting of O and CMe₂;
- Z is independently selected from the group consisting of Me, Et, and $C_3$-$C_{12}$ alkyl;
- R in this instance is independently selected from the group consisting of H, Me, Et, and $C_3$-$C_{16}$ alkyl.

4. The composition of claim 3 wherein said fluorescent compound is

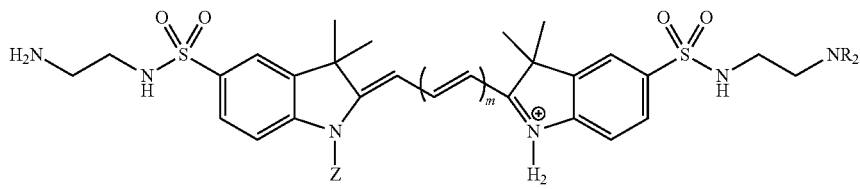

wherein:
- m is 1, 2 or 3;
- Z is independently selected from the group consisting of Me, Et, and $C_3$-$C_{12}$ alkyl;
- R in this instance is independently selected from the group consisting of H, Me, Et, and $C_3$-$C_{16}$ alkyl.

5. The composition of claim 3 wherein said fluorescent compound is

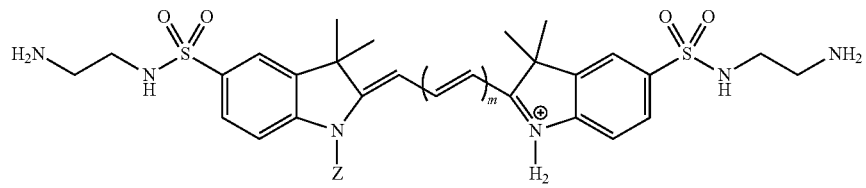

wherein:
m is 1, 2 or 3;
Z is independently selected from the group consisting of Me, Et, and $C_3$-$C_{12}$ alkyl.

6. The composition of claim 1 wherein said fluorescent compound is

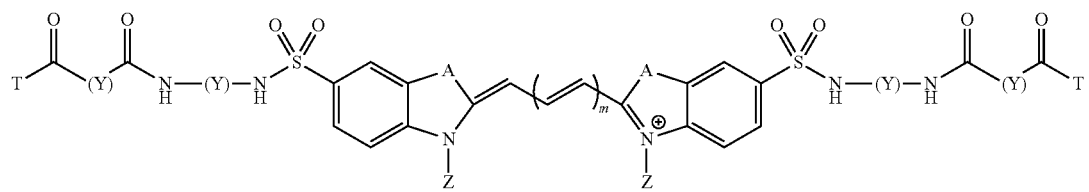

wherein:
m is 1 or 2;
A is independently selected from the group consisting of O and $CMe_2$;
Z is independently selected from the group consisting of Me, Et, and $C_3$-$C_8$ alkyl;
Y is selected from the group consisting of a $C_1$-$C_{18}$ alkyl chain, $C_1$-$C_{12}$ cycloalkyl, an ether linkage, an aromatic linkage and an oligoethylene glycol linkage containing 2 to 20 oxygen atoms,
T is independently selected from the group consisting of OH, Cl, Br, O—($C_1$-$C_{16}$) alkyl, O-aryl, N-hydroxysuccinimide ester, hydroxybenzotriazole ester, haloalkylacetamide, —NH-maleimide, thiocyanate, cyanate, phosphoramidite, symmetrical anhydrides and unsymmetrical acid anhydrides.

7. The composition of claim 1 wherein said fluorescent compound is

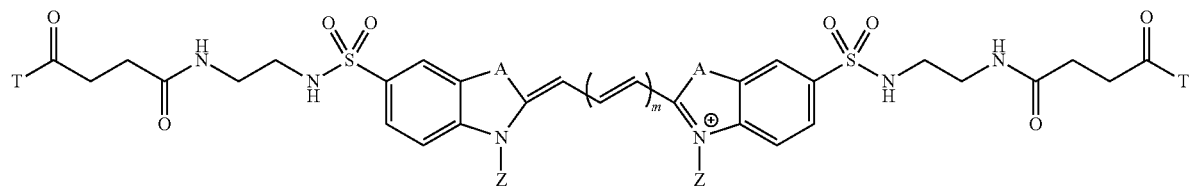

wherein:
m is 1 or 2;
A is independently selected from the group consisting of O and $CMe_2$;
Z is independently selected from the group consisting of Me, Et, and $C_3$-$C_8$ alkyl;
T is independently selected from the group consisting of OH, Cl, Br, O—($C_1$-$C_{16}$) alkyl, O-aryl, N-hydroxysuccinimide ester, hydroxybenzotriazole ester, haloalkylacetamide, —NH-maleimide, thiocyanate, cyanate, phosphoramidite, symmetrical anhydrides and unsymmetrical acid anhydrides.

8. The composition of claim 1 wherein said fluorescent compound is

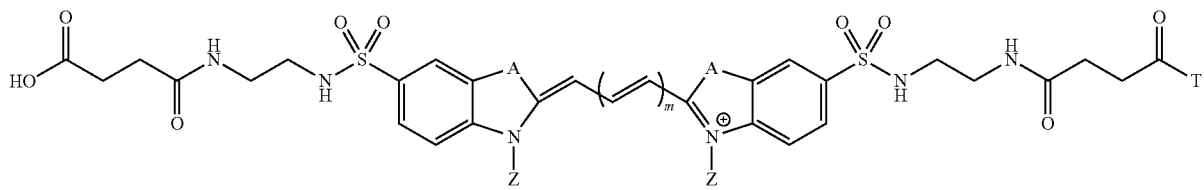

wherein:
m is 1 or 2;
A is independently selected from the group consisting of O and CMe$_2$;
Z is independently selected from the group consisting of Me, Et, and C$_3$-C$_8$ alkyl;
T is selected from the group consisting of OH Cl, Br, O—(C$_1$-C$_{16}$) alkyl, O-aryl, N-hydroxysuccinimide ester, hydroxybenzotriazole ester, haloalkylacetamide, —NH-maleimide, thiocyanate, cyanate, phosphoramidite, symmetrical anhydrides and unsymmetrical acid anhydrides.

9. The composition of claim 1 wherein said fluorescent compound is

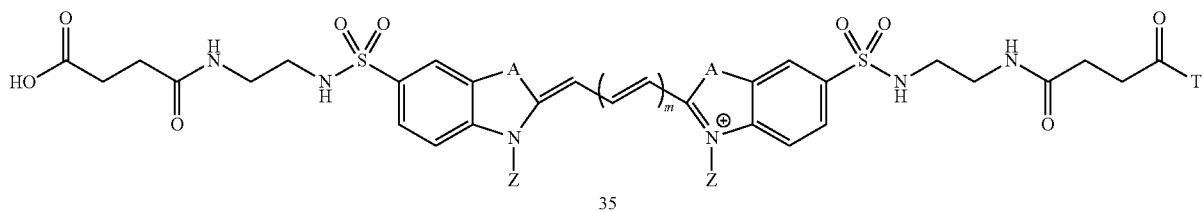

wherein:
m is 1 or 2;
Z is independently selected from the group consisting of Me, Et, and C$_3$-C$_8$ alkyl;
T is selected from the group consisting of OH Cl, Br, O—(C$_1$-C$_{16}$)alkyl, O-aryl, N-hydroxysuccinimide ester, hydroxybenzotriazole ester, haloalkylacetamide, —NH-maleimide, thiocyanate, cyanate, phosphoramidite, symmetrical anhydrides and unsymmetrical acid anhydrides.

10. The composition of claim 1 wherein said fluorescent compound is

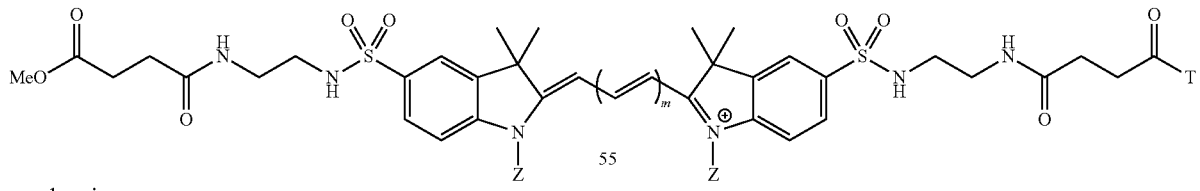

wherein:
m is 1 or 2;
Z is independently selected from the group consisting of Me, Et, and C$_3$-C$_8$ alkyl;
T is selected from the group consisting of OH Cl, Br, O—(C$_1$-C$_{16}$)alkyl, O-aryl, N-hydroxysuccinimide ester, hydroxybenzotriazole ester, haloalkylacetamide, —NH-maleimide, thiocyanate, cyanate, phosphoramidite, symmetrical anhydrides and unsymmetrical acid anhydrides.

\* \* \* \* \*